United States Patent [19]
Hamann et al.

[11] Patent Number: 5,962,708
[45] Date of Patent: *Oct. 5, 1999

[54] PROCESS FOR PREPARATION OF HIGHLY CONCENTRATED FREE-FLOWING AQUEOUS SOLUTIONS OF BETAINES

[75] Inventors: Ingo Hamann, Bad Orb; Hans-Jurgen Kohle, Schlüchtern; Winfried Wehner, Neubof, all of Germany

[73] Assignee: Witco Surfactants GmbH, Steinau an der Strasse, Germany

[*] Notice: This patent is subject to a terminal disclaimer.

[21] Appl. No.: 08/977,939

[22] Filed: Nov. 24, 1997

Related U.S. Application Data

[63] Continuation of application No. 08/629,231, Apr. 8, 1996, abandoned.

[30] Foreign Application Priority Data

Apr. 29, 1995 [DE] Germany .................. 195 15 883

[51] Int. Cl.$^6$ .................................................. C07C 231/00
[52] U.S. Cl. ........................... 554/69; 252/355; 252/357; 252/546; 252/DIG. 7; 510/123; 510/158; 510/490; 510/535; 560/1; 560/100; 560/110; 560/122; 560/253; 562/553; 554/52; 554/68; 564/138; 564/141

[58] Field of Search .................. 554/52, 68, 69; 560/1, 100, 110, 253, 122; 562/553; 252/546, DIG. 7, 355, 357; 564/138, 141; 510/535, 123, 158, 490

[56] References Cited

U.S. PATENT DOCUMENTS

| | | | |
|---|---|---|---|
| 4,832,871 | 5/1989 | Bade ........................................ | 252/546 |
| 5,354,906 | 10/1994 | Weitemeyer et al. ..................... | 554/52 |
| 5,464,565 | 11/1995 | Hamann et al. ......................... | 252/546 |
| 5,470,992 | 11/1995 | Gruning et al. .......................... | 554/69 |
| 5,681,972 | 10/1997 | Hamann et al. ......................... | 554/69 |

*Primary Examiner*—Shailendra Kumar
*Attorney, Agent, or Firm*—Scully, Scott, Murphy & Presser

[57] ABSTRACT

The invention relates to a process for the preparation of highly concentrated free-flowing and pumpable aqueous solutions of betaines by quaternization of a compound which contains tertiary amine nitrogen with a ω-halo carboxylic acid characterized in that 0.5–5% by weight of the final product, of a viscosity-reducing compound such as an alkali or alkaline earth metal citric acid salt is added to the reaction mixture before or during the quaternization reaction.

16 Claims, No Drawings

PROCESS FOR PREPARATION OF HIGHLY CONCENTRATED FREE-FLOWING AQUEOUS SOLUTIONS OF BETAINES

This application is a continuation of application Ser. No. 08/629,231 filed Apr. 8, 1996, now abandoned.

FIELD OF THE INVENTION

The invention relates to a process for the preparation of highly concentrated free-flowing aqueous solutions of betaines which contain solids contents of up to 50% by weight.

Betaines have become established in recent years in the cosmetics industry as a regular ingredient of formulations, in particular for hair and body cleansing. They have the ability to form a dense and creamy foam which remains stable over a long period, even in the presence of other surfactants, soaps and additives, associated with cleansing properties which are acknowledged to be good without any irritant side effects, even on sensitive skin.

DISCUSSION OF THE PRIOR ART

The preparation of betaines is described in detail in the relevant patent and specialist literature (U.S. Pat. No. 3,225,074). In general, this entails compounds which contain tertiary amine nitrogen atoms being reacted with ω-halo carboxylic acids or their salts in aqueous or water-containing media. The particularly used compounds which contain tertiary amine nitrogen atoms are fatty acid amides of the general formula (I)

$$R^3\text{—CONH—}(CH_2)_m\text{—}NR^4R^5 \qquad (I)$$

in which $R^3$ is the alkyl or alkenyl radical of a fatty acid, which radical is optionally branched, and can contain optionally one or more (preferably 1–5) carbon—carbon double bonds and optionally one or more hydroxyl groups, $R^4$ and $R^5$ are the same or different alkyl radicals with 1–4 carbon atoms, and m is 1–3.

In this connection, the radical $R^3$ can be derived from the natural or synthetic fatty acids with 6–20 carbon atoms, preferably from the natural vegetable or animal fatty acids with 8–18 carbon atoms, as well as their naturally occurring specifically adjusted mixtures with one another or among one another.

Examples of suitable fatty acids are caproic acid, caprylic acid, capric acid, lauric acid, palmitic acid, stearic acid, linoleic acid, linolenic acid and ricinoleic acid.

The naturally occurring fatty acid mixtures with a chain length of 8–18 carbon atoms, such as coconut fatty acid or palm kernel fatty acid, which may optionally be hardened by suitable hydrogenation methods, are preferred.

These fatty acids or fatty acid mixtures can be converted by conventional condensation reaction at 140–200° C. with one or more amines of the general formula (II)

$$H_2N\text{—}(CH_2)_m\text{—}NR^4R^5 \qquad (II)$$

in which $R^4$ and $R^5$ and m have the meaning specified in the formula (I)—to the fatty acid amides with tertiary nitrogen atoms of the general formula (I).

The subsequent quaternization reaction to give betaines of the formula (III)

$$R^3\text{—CONH—}(CH_2)_m\text{—}N^+R^4R^5(CH_2)_yCOO^- \qquad (III)$$

in which $R^3, R^4, R^5$ and m have the same meaning as in the formulae (I) and (II) and y can be 1, 2 or 3, can be carried out by processes known from the literature.

As a rule, this entails adding to the fatty acid amide of the formula (I) in aqueous medium one or more ω-haloalkylcarboxylic acids, preferably the sodium salt of chloroacetic acid, and completing the quaternization in a reaction at about 80–100° C. for several hours. Depending on the fatty acid or fatty acid mixture used it is necessary, in order to maintain stirrability as the reaction advances, for a minimum amount of water to be present. The commercially customary concentration of betaine content in the solutions prepared in this way is therefore about 30% by weight or below.

To save storage and transport costs as well as for formulation technological reasons in further processing, however, in many cases a higher concentration has been urgently required.

In the past therefore a number of processes intended to solve this problem have been proposed. Thus, DE-C 3 613 944 discloses a process in which the quaternization is carried out in an organic polar solvent with a water content of 20% by weight, and then the solvent is removed wholly or partly by distillation, and then the desired concentration is adjusted again with an industrially utilizable solvent.

Apart from the fact that the process disclosed in DE-C 3 613 944 is industrially elaborate and cost-intensive, organic solvents are in many cases undesired in the further processing to cosmetic formulations.

Although the process disclosed in DE-C 3 726 322 does without organic solvents, the amount of water needed for the quaternization reaction must be removed again from the reaction product by distillation, and the pH of the solution must be adjusted by relatively large amounts of acid to values of 1–4.5, which are untypical of the skin, before or after the adjustment to the desired concentration.

According to EP-A-O 353 580, nonionic, water-soluble surfactants are added to the reaction mixture composed of fatty acid amide and haloalkylcarboxylic acid before or during the quaternization reaction or to the resulting solution of the betaine, in amounts such that the finished solution contains 3–20% by weight of water-soluble surfactants.

Polyoxyethylene ethers are used as nonionic surfactants and must, for adequate solubility in water, contain 10–250 oxyethylene units.

Polyoxyethylene ethers with relatively high contents of oxyethylene units have, however, proven to be not without problems in respect of their biodegradability.

There has therefore continued to be a need for highly concentrated, free-flowing and pumpable, aqueous solutions of betaines which are free of lower alcohols such as methanol, ethanol, propanol or isopropanol.

BRIEF SUMMARY OF THE INVENTION

It has now been found, surprisingly, that free-flowing and pumpable, in some cases up to about 50 percent by weight solutions of betaines, based on dry matter, can be prepared from the reaction mixture fatty acid amide and ω-haloalkylcarboxylic acid by adding alkali metal and/or alkaline earth metal salts of organic acids, especially polybasic acids such as citric acid, before or during the quaternization reaction.

The invention therefore relates to a process for preparing highly concentrated free-flowing and pumpable aqueous solutions of betaines by quaternizing one or more compounds which contain tertiary amine nitrogen with ω-halo carboxylic acids, wherein 0.5–5% by weight of the final product, of a viscosity-reducing compound is added to the reaction mixture before or during the quaternization reaction.

DETAILED DESCRIPTION OF THE INVENTION

The process according to the invention can be carried out by mixing the ω-halo carboxylic acid and the organic acid or acids and neutralizing with at least one lithium, sodium, potassium, magnesium or calcium hydroxide, and carrying out the quaterization reaction of the compound (I) by reaction in an aqueous medium at 80–100° C. for several hours.

Another process variant for preparing highly concentrated free-flowing and pumpable aqueous solutions of betaines comprises carrying out the reaction with chloroacetic acid and one or more hydroxides of alkali metal or alkaline earth metal, or with the alkali metal and/or alkaline earth metal salt of chloroacetic acid, with the modification that one or more of the lithium, sodium, potassium, magnesium or calcium salts of citric acid, alone or in a mixture, are added as viscosity regulators before or during the quaternization reaction.

The invention therefore furthermore relates to a process for the preparation of highly concentrated free-flowing and pumpable aqueous solutions of betaines by quaternization of compounds which contain tertiary amine nitrogen with ω-halo carboxylic acids, which is characterized in that 0.5–5% by weight of the complete reaction mixture, of at least one of the compounds $$(Li^{1+})_a(X^{n-})_b, (Na^{1+})_a(X^{n-})_b, (K^{1+})_a(X^{n-})_b, (Mg^{2+})_a(X^{n-})_b, (Ca^{2+})_a(X^{n-})_b$$

in which $X^{n-}$ is the radical of an organic or inorganic acid, n is 1–3, and in the molecules with monovalent cations the value of $a^+ = b \cdot n^{31}$ and in the molecules with divalent cations the value of $a^+ = (b \cdot n^-)/2$, is added to the fatty acid amide of the general formula (I) and the alkali metal/alkaline earth metal salt of the ω-halo carboxylic acid before or during the quaternization reaction.

$X^{n-}$ is the anion of mono- or polybasic organic acids, in particular mono- to tribasic acids, as long as they form soluble salts with Li, Na, K, Mg, Ca, preferably acetic acid or citric acid. Additional useful acids have the formula HOOC—$(CH_2)_n$—COOH, wherein n is 0–10, such as adipic, azelaic and sebacic acids.

Preferably used according to the invention are, however, Na citrate, K citrate, Li citrate, Mg citrate, and/or Ca citrate in the form of the anhydrous salts or of the hydrates.

The amount of the viscosity-reducing salt to use is between 0.5–5% by weight, based on the complete mixture, preferably between 1.5–2.5% by weight. The upper limit is not critical, but amounts which are too large should be avoided because, in the final analysis, they reduce the active content.

Another process variant comprises replacing the $Li^+$, $Na^+$, $K^+$, $Mg^{2+}$ and $Ca^{2+}$ salts of the organic acids wholly or partly—preferably from 30–70% by weight—by one or more compounds of the general formula (IV)

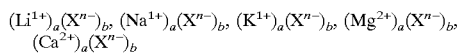

(IV)

in which R, $R^1$, $R^2$ are identical or different and each is an alkyl radical which is straight or branched and optionally contains 1 to 3 hydroxyl groups, and each contains 1–10 carbon atoms, in particular methyl radicals; and n is 1–3 and is preferably 1. Preferred mixtures according to the invention comprise 0.5–2% by weight of the viscosity regulating salt and 0.5–5% by weight of betaine (IV).

Compounds of the general formula (IV) which are used according to the invention are, for example, the products of quaternization of dimethylethanolamine, methyldiethanolamine or ($C_2$–$C_{10}$) alkyl dimethylamine, with monochloroacetic acid, but particularly trimethylglycine or "betaine" which occurs naturally in sugarbeet (*Beta vulgaris*).

These compounds can be added as mixtures together with the salts, in parallel with the addition of the salts or after the addition of the salts in amounts of 1–5% by weight, based on the aqueous solution, to the reaction mixture, there being no advantages as a rule from a total content of (salt plus betaine) exceeding about 5–7% by weight based on the aqueous solution.

Mixtures of 0.5–2% by weight of salt and 0.5–5% by weight of betaine are preferred according to the invention.

The procedure for the process is based on quaternization processes known in the prior art, the essential modification to the prior art comprising the addition of the alkali metal and/or alkaline earth metal salts of the organic acids and, where appropriate, of a compound of the general formula (IV) before or during the quaternization reaction.

The process according to the invention preferably comprises mixing the ω-halo carboxylic acid and the organic acid and neutralizing with at least one alkali metal hydroxide or alkaline earth metal hydroxide and maintaining the pH of the solution during the reaction in aqueous medium at 80–100° C. for several hours at between 8–10 by adding a base, preferably an alkali metal hydroxide, and adjusting the pH after the quaternization to a pH 4.5–6 with an organic acid, preferably citric acid.

Analytical methods

Dry matter:

The dry matter was determined by drying the material to constant weight at 105° C. These values are determined by the standard methods of the Deutsche Gesellsschaft für Fettchemie (DGF): B-II.

Acid Value (AV):

The acid value is a measure of the free acids contained in fats and technical fatty acids. It indicates the number of milligrams of potassium hydroxide necessary to neutralize 1 gram of substance or technical fatty acids (mg KOH/g). These values are determined by the standard methods of the Deutsche Gesellschaft für Fettchemie (DGF): D-IV 2a.

Ester value (EV):

The ester value is a measure of the esters contained in fats and technical fatty acids. It indicates the number of milligrams of potassium hydroxide necessary to hydrolyze 1 gram of substance or technical fatty acids (mg KOH/g). These values are determined by the standard methods of the Deutsche Gesellschaft fur Fettchemie (DGF): C-V 4.

Total amine value (TAV), tertiary amine value (tAV):

The total amine value indicates the number of milligrams of potassium hydroxide equivalent to the total basicity of 1 gram of the amine compound (mg KOH/g).

The tertiary amine value indicates the number of milligrams of potassium hydroxide equivalent to the tertiary amine basicity of 1 gram of the amine compound (mg KOH/g).

The values are determined by the American Oil Chemists Society (A.O.C.S.) Official Method Tf 2a-64.

Chloride:

The chloride content is measured potentiometrically with a reference silver nitrate standard solution. A combined silver chloride electrode is used as electrode. The values are determined by the standard methods of the Deutsche Gesellschaft für Fettchemie (DGF): H-III 9.

The following examples are provided for purposes of illustration and are not intended to limit the scope of that which is regarded as the invention.

EXAMPLE 1

Preparation of the amine amide:

98.0 g of hardened coconut oil were mixed with 56.8 g of dimethylaminopropylamine in a reactor with stirrer, thermometer and distillation head under an inert gas atmosphere and heated to 150–160° C. and boiled under reflux. After the amidation was complete (ester value <10 mg KOH/g), the excess amine was distilled off in vacuo at this temperature. The distillation was complete when the difference between the total amine value and the tertiary amine value was less than 3 mg KOH/g. The resulting amine amide had a TAV of 170.6 mg KOH/g, a tAV of 168.6 mg KOH/g and an ester value of 2.8 mg KOH/g.

EXAMPLE 2

97.3 g of monochloracetic acid were diluted with 500 g of water while cooling in a 1 liter flask with stirrer, internal thermometer and pH electrode and, after addition of 25.2 g of the trisodium salt of citric acid dihydrate, cautiously neutralized with 85 g of 50% strength aqueous NaOH solution. After addition of 325 g of the amine amide from Example 1, the reaction mixture was stirred at 80–90° C. During this time the pH was kept between 8 and 8.5. A further 5.5 g of 50% strength aqueous NaOH solution in total were required for this. The alkylation was complete after a reaction time of about 9 hours. The betaine mixture which resulted was allowed to cool to 50° C., and the pH was adjusted to 5.4 with 5.3 g of citric acid monohydrate.

The final product was a clear solution with a viscosity of 145 mPas at 20° C., a residue on drying of 45.5% and a chloride content of 3.7%.

EXAMPLE 3

97.3 g of monochloroacetic acid were diluted with 500 g of water while cooling in a 1 liter flask with stirrer, internal thermometer and pH electrode and, after addition of 11.2 g of the trisodium salt of citric acid dihydrate, cautiously neutralized with 85 g of 50%, strength aqueous NaOH solution. After addition of 12 g of trimethylglycine and 325 g of the amine amide from Example 1, the reaction mixture was stirred at 80–90° C. During this time was kept between 8 and 8.5. A further 5.5 g of 50% strength aqueous NaOH solution in total were required for this. The alkylation was complete after a reaction time of about 8 hours. The betaine mixture which resulted was allowed to cool to 50° C., and the pH was adjusted to 5.8 with 4 g of citric acid monohydrate.

The final product was a clear solution with a viscosity of 140 mPas at 20° C., a residue on drying of 45.2% and a chloride content of 3.5%.

EXAMPLE 4

97.3 g of monochloroacetic acid were diluted with 500 g of water while cooling in a 1 liter flask with stirrer, internal thermometer and pH electrode. 7.2 g of a magnesium salt of citric acid were added and the mixture was cautiously neutralized with 35 g of magnesium hydroxide. After addition of 325 g of the amine amide from Example 1, the reaction mixture was stirred at 80–90° C. During this time the pH was kept at between 8 and 8.5. A further 2.9 g of magnesium hydroxide in total were required for this. The alkylation was complete after a reaction time of about 8 hours. The betaine mixture which resulted was allowed to cool to 50° C. The pH was adjusted to 5.1 with 6.5 g of 50% strength citric acid solution.

The final product was a clear liquid with a viscosity of 90 mPas at 20° C., a residue on drying of 45.6% and a chloride content of 3.6%.

EXAMPLE 5

97.3 g of monochloroacetic acid were diluted with 460 g of water while cooling in a 1 liter flask with stirrer, internal thermometer of pH electrode. 17 g of a magnesium salt of citric acid were added and the mixture was cautiously neutralized with 38.0 of magnesium hydroxide. After addition of 325 g of the amine amide from Example 1, the reaction mixture was stirred at 80–90° C. During this time the pH was kept at between 8 and 8.5. A further 5.0 g of 50% strength aqueous NaOH solution in total were required for this. The alkylation was complete after a reaction time of about 8 hours. The betaine mixture which resulted was allowed to cool to 50° C. The pH was adjusted to 5.7 with 4 g of citric acid monohydrate.

The final product was a clear liquid with a viscosity of 190 mPas at 20° C., a residue on drying of 49.8% and a chloride content of 3.9%.

What is claimed is:

1. A process for preparing a highly concentrated free-flowing and pumpable aqueous solution of betaine comprising at least 45 wt. % water, comprising (a) quaternizing a compound which contains tertiary amine nitrogen with ω-halo carboxylic acid in an aqueous medium, and (b) adding 0.5–5% by weight of the final product, of a viscosity-reducing compound to the reaction mixture before or during the quaternization reaction.

2. A process for preparing a highly concentrated free-flowing and pumpable aqueous solution of betaine, comprising (a) quaternizing a fatty acid amide of the general formula I $$R^3\text{—CONH—}(CH_2)_m\text{—}NR^4R^5 \qquad (I)$$

wherein $R^3$ is alkyl or alkenyl containing 6 to 20 carbon atoms and 0 to 5 carbon—carbon double bonds, m is 1–3, and $R^4$ and $R^5$ are the same or different and each is alkyl containing 1–4 carbon atoms, with a salt selected from the group consisting of alkaline earth metal salts of ω-halo carboxylic acid in an aqueous medium, and (b) adding 0.5–5% by weight of the complete mixture, of at least one salt compound of the formula

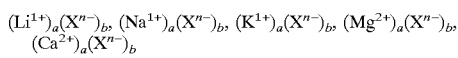

in which $X^{n-}$ is the radical of an organic acid, in the molecules with monovalent cations the value of $a=b\cdot n^-$ and in the molecules with divalent cations the value of $a=(b\cdot n^-)/2$, and n is 1–3, before or during the quaternization reaction.

3. A process according to claim 1, wherein step (b) comprises adding 1.5–2.5% by weight of the final product, of one more salts of citric acid whereby the viscosity of the reaction mixture is reduced.

4. A betaine solution prepared according to claim 1, wherein said solution contains a salt component selected from the group consisting of lithium, sodium, potassium, magnesium and calcium salts and mixtures thereof, in an amount of 30–100 equivalent %.

5. A betaine solution prepared according to claim 4, wherein said solution contains more than 35% by weight of compounds of the general formula (III)

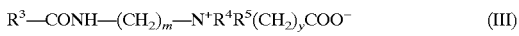

$$R^3—CONH—(CH_2)_m—N^+R^4R^5(CH_2)_yCOO^- \quad (III)$$

wherein $R^3$ is alkyl or alkenyl containing 6 to 20 carbon atoms and 0 to 5 carbon—carbon double bonds, m is 1–3, $R^4$ and $R^5$ are the same or different and each is alkyl containing 1–4 carbon atoms, and y is 1–3; 1.5–3% by weight of at least one lithium, sodium, potassium, magnesium or calcium salt; add 100 water.

6. A betaine solution according to claim 5, wherein said solution contains salt of citric acid.

7. A process according to claim 3 wherein 30–70% by weight of said at least one salt compound present is replaced by one or more compounds of the general formula (IV)

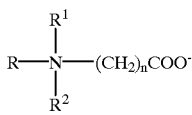

(IV)

in which R, $R^1$ and $R^2$ are the same or different and each is a straight or branched alkyl radical containing 1 to 10 carbon atoms and each optionally contains up to 3 hydroxyl groups, and n is 1–3.

8. A process according to claim 1 wherein said viscosity-reducing compound is a salt of a mono- or polybasic organic acid.

9. A process according to claim 1 wherein said viscosity-reducing compound is a salt of a polybasic organic acid.

10. A process according to claim 2, wherein step (b) comprises adding 1.5–2.5% by weight of the final product, of one more salts of citric acid whereby the viscosity of the reaction mixture is reduced.

11. A betaine solution prepared according to claim 2, wherein said solution contains a salt component selected from the group consisting of lithium, sodium, potassium, magnesium and calcium salts and mixtures thereof, in an amount of 30–100 equivalent %.

12. A betaine solution prepared according to claim 11, wherein said solution contains more than 35% by weight of compounds of the general formula (III)

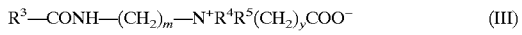

$$R^3—CONH—(CH_2)_m—N^+R^4R^5(CH_2)_yCOO^- \quad (III)$$

wherein $R^3$ is alkyl or alkenyl containing 6 to 20 carbon atoms and 0 to 5 carbon—carbon double bonds, m is 1–3, $R^4$ and $R^5$ are the same or different and each is alkyl containing 1–4 carbon atoms, and y is 1–3; 1.5–3% by weight of at least one lithium, sodium, potassium, magnesium or calcium salt; ad 100 water.

13. A betaine solution according to claim 12, wherein said solution contains salt of citric acid.

14. A process according to claim 2 wherein 30–70% by weight of said at least one salt compound present is replaced by one or more compounds of the general formula (IV)

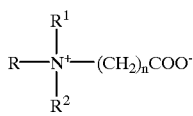

(IV)

in which R, $R^1$ and $R^2$ are the same or different and each is a straight or branched alkyl radical containing 1 to 10 carbon atoms and each optionally contains up to 3 hydroxyl groups, and n is 1–3.

15. A process according to claim 2 wherein said salt compound is a salt of a mono- or polybasic organic acid.

16. A process according to claim 2 wherein said salt compound is a salt of a polybasic organic acid.

* * * * *